United States Patent [19]

Greenway et al.

[11] Patent Number: 4,606,338

[45] Date of Patent: Aug. 19, 1986

[54] SLIP RESISTANT BANDAGE

[75] Inventors: J. Michael Greenway, Westwood; Peter J. Schoots, Walpole, both of Mass.; Donald Patience, Cary, Ill.

[73] Assignee: The Kendall Company, Boston, Mass.

[21] Appl. No.: 731,185

[22] Filed: May 6, 1985

[51] Int. Cl.4 .............................................. A61L 15/00
[52] U.S. Cl. ................................................... 128/156
[58] Field of Search .................... 128/156, 296, 290 R

[56] References Cited

U.S. PATENT DOCUMENTS

| | | | |
|---|---|---|---|
| 4,214,582 | 7/1980 | Patel | 128/156 |
| 4,302,500 | 11/1981 | Flora | 128/156 |
| 4,373,519 | 2/1983 | Errede | 128/156 |

Primary Examiner—Gregory E. McNeill
Attorney, Agent, or Firm—Edward J. Scahill, Jr.

[57] ABSTRACT

A bandage comprising a fabric formed from at least one layer of nonwoven hydroentangled fibers having a skim coat of adhesive disposed thereon. Subsequent to entangling the fibers, the fabric is compacted to arrange the fabric into a series of wave-like configurations having crests and valleys. These wave-like configurations allow the fabric to stretch when pulled, and recover to most of its original form when the tension is released. After compacting, a light coat of adhesive is applied to the crests of the fabric to impart some slip resistance to the surface of the fabric while leaving the valleys substantially free from adhesive. The adhesive may be applied to one side or both sides of the fabric, depending on the requirements of the fabric. The thusly formed bandage, when stretched for application, has discontinuous areas of adhesives disposed therein that provide sufficient slip resistance while also permitting complete repositionability.

16 Claims, 2 Drawing Figures

HEATED MAIN ROLL

HEATED MAIN ROLL

SLIP RESISTANT BANDAGE

BACKGROUND OF THE INVENTION

This invention relates to bandages, and more particularly to bandages that have some degree of self adherency that will not slip or loosen with time when applied to a patient.

Traditionally, elastic bandages made with elastic yarns are used to wrap a patient. Elastic bandages have an inherent built-in in ability to slip when wrapped on a patient, because the elastic yarns want to return to their normal and relaxed state. If the elastic bandage is wrapped tight it inevitably causes circulatory deficiencies in a patient.

A very important functional property of a bandage therefore is its the ability to cling to itself or not slip or loosen with time after it has been applied to a patient. In most conditions, foreign matter, such as metal clamps or other types of fasteners, have to be used in order to hold a bandage in place, but usually do not keep the bandage from slipping.

The present invention has overcome the aforementioned prior art deficiencies by producing a compacted hydroentangled fabric exhibiting some stretchablity with a small amount of adhesive applied on the crests of pleats, created by the compacting, of the fabric. The compacting also allows the fabric to be stretched and to recover when the tension is released. Thus, when the fabric is stretched the adhesive on the crests may appear at random points throughout the fabric. The applied adhesive, depending on whether it is applied to one or both surfaces of the fabric, gives the surface or surfaces of the fabric a slip resistance property. This keeps the bandage in place when it has been applied to a patient.

In U.S. Pat. No. 3,575,782, there is described a covering material that consists of partially extended spaced-aligned elastic yarns sealed between two thin porous gathered nonwoven fibrous webs or between a web and a non-porous film by means of a soft, flexible polymeric coherent binder. The soft, flexible polymeric coherent binder provides the self adherent character to the wrap that prevents the prior art bandage from slipping or loosening with time after being applied to a patient. A disadvantage with this prior art is that it has numerous process steps which makes it very expensive to produce. One other disadvantage is that the prior art is made with elastic yarn, thus, when the bandage is wrapped around a patient, it may cause circulatory deficiencies, due to the tension needed in wrapping the bandage to keep it in place.

The present invention because it is made from a compacted nonwoven hydroentangled fabric, is far superior to prior art, when it comes to being slip resistant and economical.

SUMMARY OF THE INVENTION

A bandage comprised of a fabric formed from at least one layer of a blend of hydroentangled cellulosic and thermoplastic fibers has an adhesive disposed thereon. Although a fabric formed by hydroentangled fibers is preferred, the bandage fabric may also be a woven material comprising the same type fibers. In the hydroentangled form, subsequent to entangling the fibers, the fabric is compacted. The compacting arranges the fabric into a series of wave-like configurations having crests and valleys. These wave-like configurations are important because they allow the fabric to have stretch when pulled, and to recover to its original form when the tension is released. After compacting, an adhesive is applied to the crests of the fabric, by a roll applicator, for example, to impart a slip resistant surface to the fabric. The adhesive may be applied to one side or both sides of the fabric, depending on the requirements of the fabric. Then, upon stretch the bandage is characterized by discontinuous areas of adhesive.

The principle object of the present invention is to provide a bandage that is substantially slip resistant when wrapped upon itself or upon the skin of a patient when the bandage is applied to a patient, but that has sufficient non-adhesive areas thereon as to permit unwrapping and repositioning the bandage after the initial application.

Other objects of the present invention will become apparent from the drawings, specification and claims.

DESCRIPTION OF PREFERRED EMBODIMENT

Figure 2:
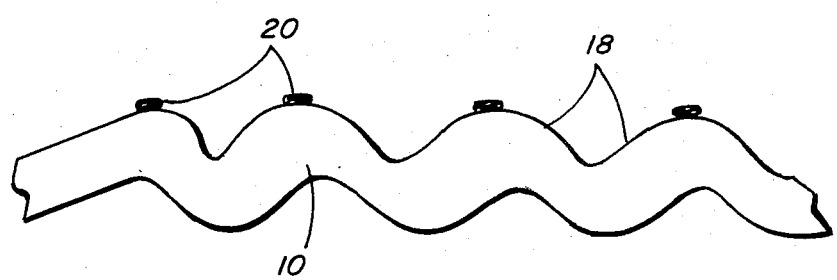
FIG. 2 is a cross sectional view illustrating the position of the adhesive on the crests of the compacted fabric.

The basic fabric of the present invention incorporates a nonwoven textile fabric such as is made in accordance with the teachings of U.S. Pat. No. 3,508,308, issued to W. W. Bunting Jr. et al on Apr. 28, 1970 and hereinafter referred to as "hydroentangled fabric". As described therein, those fabrics comprise fibers mechanically locked into place by fiber interaction to provide a strong, uniform, cohesive structure which maintains a structural integrity without the need for binders. The fabrics of entangled fibers are substantially non-patterned, generally smooth surfaced, have dense entangled regions of fibers and are strong. There are interconnecting fibers which extend between the dense entangled regions and are randomly entangled with each other in the dense entangled regions. As it is described in the aforementioned patent to Bunting, the entanglement is accomplished by first preparing a loose layer of fibers and then passing the loose layer onto a screen where it is treated with liquid jetted at high pressures from one or more rows of smaller orifices to convert the layer into an entangled nonwoven fabric. Although a hydroentangled nonwoven fabric is preferred, a woven fabric made using a combination of cotton and rayon fibers or such as that shown in U.S. Pat. No. 3,190,289, incorporated herein by reference, or other nonwoven material may be used with equally good results.

In accordance with the present invention, at least one layer of a blend of cellulosic fibers, preferably rayon, and at least 15 percent of thermoplastic fibers, preferably polyester, is formed into a hydroentangled fabric by passing the loose fiber layer through an entangler, as described above, having rows of high pressure water jets. Although one layer of blended fibers is preferred, multiple layers of various combinations of blends of fibers may be used to give variations of the fabric. In addition, the layer or layers of fabric may be 100 percent thermoplastic depending on the requirements of the bandage. However, a certain amount of hydrophilic fibers in the bandage is preferred for absorbency.

The hydroentangled nonwoven fabric so made is then compacted, such as by a Micrex machine. These compacting machines are available from Bird Machine Company in Walpole, Mass. and are sold under the trademark Micrex. This compacting procedure therefore may be referred to as micrexing the fabric. Micrexed fabric is shown in a somewhat simplified form in FIG. 1. It is there shown, that a length of hydroentangled fabric 10 is driven forward by a heated rotary main roll 12 into the nip between the main roll 12 and a pressure assembly 14. The heated main roll 12 may have a grooved surface or, as preferred a smooth, cylindrical surface. The temperature to which the main roll is heated depends on the particular fabric being micrexed. It is typically heated to preferably about 300 F. As the fabric 10 moves into the nip, the pressure assembly 14 forces the fabric toward the surface of the main roll 12 keeping it in contact with the main roll. A hard rubber element 16 is used to retard the fabric 10 as it passes underneath the pressure assembly 14. The hard rubber element not only retards the fabric but also diverts it away from the surface of the main roll 12.

Figure 1:
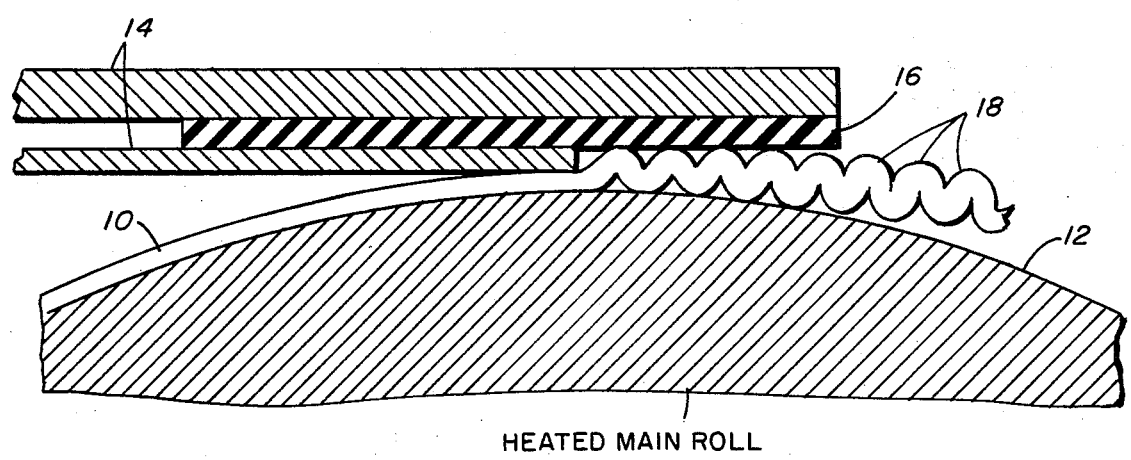
FIG. 1 is a cross sectional view of a bandage fabric being processed, in this embodiment, and the compacting apparatus.

As shown, in FIG. 1, the combined action of the main roll 12, the pressure assembly 14 and the hard rubber element 16 imparts pleats 18, having crests and valleys, to the fabric 10. The fabric 10 is squeezed or compacted in such a way as to cause the fabric to be rearranged into a repeating series of wave-like configurations extending substantially along its length and running across the width of the fabric. The pleating of the fabric takes place, due to the heat from the main roll, which softens the thermoplastic fibers in the fabric so when they contact the hard rubber element, they are formed into the pleated or wave-like form. As the fabric, in its new rearranged wave-like form, leaves the area of the heated main roll it cools and the fabric maintains its pleated form. Once the fabric has been micrexed into pleats, the so called pleated fabric is then passed under a means for depositing an adhesive only onto the crests of the wave-like forms, leaving the valleys substantially free of adhesive. This means of distributing or depositing the adhesive onto said crests may be by a roll applicator, which just kisses the top of the crests of the fabric depositing a small amount of adhesive. The amount of adhesive deposited may range between 0.1 to 10 percent by weight of fabric. To explain what is meant by "amount of adhesive deposited by weight of fabric" an example is given.

EXAMPLE A

A fabric has a weight of 50 grams per square yard (gyd2). The amount of adhesive to be deposited is 10 percent by weight of fabric. By multiplying the percent of adhesive $\times$ weight of fabric (gyd2) or $0.10 \times 50$ (gyd2) you arrive at 5 grams per square yard (gyd2) of adhesive being deposited on the fabric.

The present invention because it has a discontinuous adhesive on at least one surface, instead of a continuous coating of adhesive, not only gives the present invention a slip resistant surface, but allows the crests and valleys to separate thus enabling the present invention bandage to flex and stretch with a minute amount of tension having to be applied. If the present invention was to have a continuous coating of adhesive on one surface, the coating would cause the crests and valleys of the present invention to become coated, and not allow them to separate. If the crests and valleys could not separate the ability of the present invention to flex and stretch would be greatly diminished. The prior art bandages, unlike the present invention, have a substantially continuous coating of adhesive, more like a film on them, thus not conducive to flexing or stretching unless greater forces are applied.

Other methods of depositing an adhesive on the crests of the fabric may be used, such as spraying with perhaps slightly different results. The adhesive in the present invention may be an acrylic pressure sensitive adhesive. Although this is the preferred adhesive, other pressure sensitive adhesives or cohesive applications may be used with perhaps a slightly different slip resistant effect. FIG. 2 illustrates that an adhesive 20 is deposited on the crests 18 of the micrexed fabric 10. The adhesive 20 is deposited on the crests across the width and length of the fabric. The depositing of adhesive to the crest of the pleated fabric is a unique way of producing a slip resistant surface to at least one side of the fabric so when the fabric is applied as a bandage to a patient, the tension of the bandage is not relied upon to keep it in place. Also when the bandage is fully stretched, the adhesive 20 becomes isolated by areas of the bandage completely free from adhesive. Thus, this bandage can easily be unwrapped and repositioned on a patient. In addition, the crests and valleys of the successive wraps of the bandage may also provide a slip resistant bandage, because the crests and valleys of the bandage may interlock when wrapped over one another. Although it is preferred to deposit the adhesive only on one side of the fabric it may be deposited on both sides depending on the requirements of the fabric. In addition, the present invention, being accordian pleated, has the ability to stretch. This ability to stretch is important because it allows a slight tension to be applied to the bandage when it is being wrapped on a patient. The slight tension unexpectedly seems to assist, instead of detract from the slip resistant feature of the bandage. Naturally the tension applied is minute when compared to tension required by an elastic bandage. Thus, the tension applied in the present invention has no ill effect, such as restriction of blood flow on a patient. The bandage in the relaxed position is also an excellent slip resistant material. The bandage has an excellent slip resistant property because the addition of the adhesive on the crests of the bandage has increased the coefficient of friction of the fabric. With the increase of the coefficient of friction, the bandage will not slip when wrapped on the patient's skin or on the underneath wrap of the bandage itself.

To further illustrate the present invention examples are given, but it is not intended that the present invention be limited to other than the following claims.

EXAMPLE 1

A 38 gram per square yard web of predominantly machine direction fibers was prepared using a conventional carding system. The web consists of a blend of 50% 1.5 denier rayon fiber and 50% 1.5 denier polyester fibers. The web was entangled on one side, as described herein, using jets of water coming from orifices line in two manifolds. The carded web was carried under these jets of water on a $40 \times 44$ mesh screen. The jets being $\frac{1}{2}$ inch above the screen. The pressure of the jets of water was 400 and 800 psi respectfully. The partially entangled web was then put on a $13 \times 13$ mesh drum screen and passed under four additional manifolds having jets of water, with pressures of 1400, 1400, 1600, and 1600 psi, respectfully. The entangled web was then taken from the drum screen and passed through the nip of a pair of rolls to extract excess water from them. The fabric was then dried conventionally. The fabric was then compacted by using a Micrex compactor unit to rearrange the fabric into wave-like configurations and to achieve a 28% stretch in the fabric. An adhesive was then applied by using a spraying technique to apply very fine droplets of adhesive to the crests of the fabric's surface. Approximately 1% by weight of adhesive was applied to the bandage.

EXAMPLE 2

A 38 gram per square yard web of predominantly machine direction fibers was prepared using a conventional carding system. The web consists of a blend of 50% 1.5 denier rayon fiber and 50% 1.5 denier polyester fibers. The web was entangled as described in Example 1. The entangled web was then taken from the drum screen and passed through the nip of a pair of rolls to extract excess water from them. The fabric was then dried conventionally. The fabric was then compacted by using a Micrex compactor unit to rearrange the fabric into wave-like configurations and to achieve a 28% stretch in the fabric. An adhesive was then applied by using an application roll kiss coating technique. The adhesive was thickened to prevent it from soaking into the material so that only a small amount of adhesive was applied to the crests of the fabric's surface. Approximately 1% by weight of adhesive was applied to the bandage. A novel and useful bandage material was thus prepared.

EXAMPLE 3

This example is a gauze fabric made from cotton warp yarns, size 30 and cotton filler yarns, size 40 and having a thread count of 20×12 mesh and woven by conventional methods. The fabric was then compacted by using a Micrex compactor unit to rearrange the fabric into wave-like configurations and to achieve a 28% stretch in the fabric. An adhesive was then applied by using an application roll kiss coating technique. The adhesive was thickened to prevent it from soaking into the material so that only a small amount of adhesive was applied to the crests of the fabric's surface. Approximately 1% by weight of adhesive was applied to the bandage fabric. A novel and useful bandage material was thus prepared.

EXAMPLE 4

This example is also a gauze fabric made from cotton warp yarns, size 30 and cotton filler yarns, size 40 and having a thread count of 20×12 mesh and woven by conventional methods. The fabric was then compacted by using a Micrex compactor unit to rearrange the fabric into wave-like configurations and to achieve a 28% stretch in the fabric. An adhesive was then applied by using a spraying technique to apply very fine droplets of adhesive to the crests of the fabric's surface. Approximately 1% by weight of adhesive was applied to the bandage.

What is claimed is:

1. A bandage comprising a compacted nonwoven fabric formed from at least one layer of hydroentangled fibers, said fabric having a series of wave-like configurations having crests and valleys, said crests having an adhesive disposed thereon, on at least one surface of said fabric, said valleys being substantially free of adhesive.

2. The bandage of claim 1 wherein said fibers comprise a blend of cellulosic fiber and at least 15 percent of thermoplastic fiber.

3. The bandage of claim 2 wherein said cellulosic fiber is rayon.

4. The bandage of claim 2 wherein said thermoplastic fiber is selected from a group consisting of polyester, nylon and polypropylene fibers.

5. The bandage of claim 1 wherein said adhesive is a pressure sensitive adhesive.

6. The bandage of claim 1 wherein the amount of adhesive deposited on said crests range between 0.1 to 10 percent by weight of fabric.

7. A bandage comprising at least one layer of a woven fabric, said fabric having a series of wave-like configurations having crests and valleys, said crests, on at least one side of said fabric, having an adhesive disposed thereon, said valleys being substantially free of adhesive.

8. The bandage of claim 7 wherein said fabric comprises cotton warp and filler yarns.

9. The bandage of claim 7 wherein said adhesive is a pressure sensitive adhesive.

10. The bandage of claim 7 wherein the amount of adhesive deposited may range between 0.1 to 10 percent by weight of fabric.

11. A bandage comprising at least one layer of a nonwoven fabric, said fabric having a series of wave-like configurations having crests and valleys, said crests, on at least one side of said fabric, having an adhesive disposed thereon, said valleys being substantially free of adhesive.

12. The bandage of claim 11 wherein said fabric comprise a blend of cellulosic fiber and at least 15 percent of thermoplastic fiber.

13. The bandage of claim 12 wherein said cellulosic fiber is rayon.

14. The bandage of claim 12 wherein said thermoplastic fiber is selected from a group consisting of polyester, nylon and polypropylene fibers.

15. The bandage of claim 11 wherein said adhesive is a pressure sensitive adhesive.

16. The bandage of claim 11 wherein the amount of adhesive deposited may range between 0.1 to 10 percent by weight of fabric.

* * * * *